US007955255B2

(12) United States Patent
Boulais et al.

(10) Patent No.: US 7,955,255 B2
(45) Date of Patent: Jun. 7, 2011

(54) IMAGING ASSEMBLY WITH TRANSPARENT DISTAL CAP

(75) Inventors: Dennis R. Boulais, Danielson, CT (US); Michael S. Banik, Bolton, MA (US); William Lucas Churchill, Bolton, MA (US); Sergey S. Grigoryants, Medford, MA (US); Louis J. Barbato, Franklin, MA (US); Daniel G. Orband, Boxford, MA (US); Luis J. Maseda, Natick, MA (US); Stephen D. Fantone, Lynnfield, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 542 days.

(21) Appl. No.: 11/407,700

(22) Filed: Apr. 20, 2006

(65) Prior Publication Data
US 2007/0249907 A1 Oct. 25, 2007

(51) Int. Cl.
*A61B 1/06* (2006.01)
(52) U.S. Cl. ........ 600/177; 600/129; 600/156; 600/160; 600/176
(58) Field of Classification Search ............... 600/104, 600/109, 117, 118, 128–130, 132, 154, 155–160, 600/175–179, 153
See application file for complete search history.

(56) References Cited

U.S. PATENT DOCUMENTS

| 3,266,059 A | 8/1966 | Stelle |
| 3,470,876 A | 10/1969 | Barchilon |
| 3,572,325 A | 3/1971 | Bazell et al. |
| 3,581,738 A | 6/1971 | Moore |
| 4,108,211 A | 8/1978 | Tanaka |
| 4,286,585 A | 9/1981 | Ogawa |
| 4,294,162 A | 10/1981 | Fowler et al. |
| 4,311,134 A | 1/1982 | Mitsui et al. |
| 4,315,309 A | 2/1982 | Coli |
| 4,351,323 A | 9/1982 | Ouchi et al. |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,493,537 A | 1/1985 | Nakahashi |
| 4,495,134 A | 1/1985 | Ouchi et al. |
| 4,499,895 A | 2/1985 | Takayama |
| 4,503,842 A | 3/1985 | Takayama |
| 4,513,235 A | 4/1985 | Acklam et al. |
| 4,515,444 A | 5/1985 | Prescott et al. |
| 4,516,063 A | 5/1985 | Kaye et al. |
| 4,519,391 A | 5/1985 | Murakoshi |

(Continued)

FOREIGN PATENT DOCUMENTS
DE 87 14 480 U1 4/1988
(Continued)

*Primary Examiner* — John P Leubecker
*Assistant Examiner* — Samuel Candler
(74) *Attorney, Agent, or Firm* — Finnegan, Henderson, Farabow, Garrett & Dunner, LLP

(57) ABSTRACT

An imaging assembly for use in a medical imaging device such as an endoscope or the like. In one embodiment, the imaging assembly includes a transparent distal cap that is shaped to receive an image sensor insert. The image sensor insert has a cooling channel that supplies a cooling liquid or gas to one or more illumination sources.

13 Claims, 4 Drawing Sheets

U.S. PATENT DOCUMENTS

| | | |
|---|---|---|
| 4,552,130 A | 11/1985 | Kinoshita |
| 4,559,928 A | 12/1985 | Takayama |
| 4,566,437 A | 1/1986 | Yamaguchi |
| 4,573,450 A | 3/1986 | Arakawa |
| 4,580,210 A | 4/1986 | Nordstrom |
| 4,586,923 A | 5/1986 | Gould et al. |
| 4,615,330 A | 10/1986 | Nagasaki et al. |
| 4,616,630 A | 10/1986 | Arakawa |
| 4,617,915 A | 10/1986 | Arakawa |
| 4,618,884 A | 10/1986 | Nagasaki |
| 4,621,618 A | 11/1986 | Omagari et al. |
| 4,622,584 A | 11/1986 | Nagasaki et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,652,916 A | 3/1987 | Suzaki et al. |
| 4,654,701 A | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okobe |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,816,909 A | 3/1989 | Kimura et al. |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,836,187 A | 6/1989 | Iwakoshi et al. |
| 4,844,052 A | 7/1989 | Iwakoshi et al. |
| 4,844,071 A | 7/1989 | Chen et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,897,789 A | 1/1990 | King et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,959,710 A | 9/1990 | Uehara et al. |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,074,861 A | 12/1991 | Schneider et al. |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi |
| 5,174,293 A | 12/1992 | Hagiwara |
| 5,176,629 A | 1/1993 | Kullas et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |

| | | | | | | |
|---|---|---|---|---|---|---|
| 5,325,845 A | 7/1994 | Adair et al. | | 5,821,920 A | 10/1998 | Rosenberg et al. |
| 5,331,551 A | 7/1994 | Tsuruoka et al. | | 5,823,948 A | 10/1998 | Ross, Jr. et al. |
| 5,342,299 A | 8/1994 | Snoke et al. | | 5,827,186 A | 10/1998 | Chen et al. |
| 5,347,989 A | 9/1994 | Monroe et al. | | 5,827,190 A | 10/1998 | Palcic et al. |
| 5,374,953 A | 12/1994 | Sasaki et al. | | 5,828,197 A | 10/1998 | Martin et al. |
| 5,379,757 A | 1/1995 | Hiyama et al. | | 5,828,363 A | 10/1998 | Yaniger et al. |
| 5,381,782 A | 1/1995 | DeLaRama et al. | | 5,830,124 A | 11/1998 | Suzuki et al. |
| 5,390,662 A | 2/1995 | Okada | | 5,830,128 A | 11/1998 | Tanaka |
| 5,400,769 A | 3/1995 | Tanii et al. | | 5,836,869 A | 11/1998 | Kudo et al. |
| 5,402,768 A | 4/1995 | Adair | | 5,837,023 A | 11/1998 | Koike et al. |
| 5,402,769 A | 4/1995 | Tsuji | | 5,840,014 A | 11/1998 | Miyano et al. |
| 5,409,485 A | 4/1995 | Suda | | 5,841,126 A | 11/1998 | Fossum et al. |
| 5,412,478 A | 5/1995 | Ishihara et al. | | 5,843,000 A | 12/1998 | Nishioka et al. |
| 5,418,649 A | 5/1995 | Igarashi | | 5,846,183 A | 12/1998 | Chilcoat |
| 5,420,644 A | 5/1995 | Watanabe | | 5,855,560 A | 1/1999 | Idaomi et al. |
| 5,431,645 A | 7/1995 | Smith et al. | | 5,857,963 A | 1/1999 | Pelchy et al. |
| 5,434,615 A | 7/1995 | Matsumoto | | 5,865,724 A | 2/1999 | Palmer et al. |
| 5,436,640 A | 7/1995 | Reeves | | 5,868,664 A | 2/1999 | Speier et al. |
| 5,436,767 A | 7/1995 | Suzuki et al. | | 5,868,666 A | 2/1999 | Okada et al. |
| 5,440,341 A | 8/1995 | Suzuki et al. | | 5,871,440 A * | 2/1999 | Okada ............ 600/129 |
| 5,464,007 A | 11/1995 | Krauter et al. | | 5,873,816 A | 2/1999 | Kagawa et al. |
| 5,469,840 A | 11/1995 | Tanii et al. | | 5,873,866 A | 2/1999 | Kondo et al. |
| 5,473,235 A | 12/1995 | Lance et al. | | 5,876,326 A | 3/1999 | Takamura et al. |
| 5,482,029 A | 1/1996 | Sekiguchi et al. | | 5,876,331 A | 3/1999 | Wu et al. |
| 5,484,407 A | 1/1996 | Osypka | | 5,876,373 A | 3/1999 | Giba et al. |
| 5,485,316 A | 1/1996 | Mori et al. | | 5,876,427 A | 3/1999 | Chen et al. |
| 5,496,260 A | 3/1996 | Krauter et al. | | 5,877,819 A | 3/1999 | Branson |
| 5,515,449 A | 5/1996 | Tsuruoka et al. | | 5,879,284 A | 3/1999 | Tsujita |
| 5,518,501 A | 5/1996 | Oneda et al. | | 5,880,714 A | 3/1999 | Rosenberg et al. |
| 5,518,502 A | 5/1996 | Kaplan et al. | | 5,882,293 A | 3/1999 | Ouchi |
| 5,543,831 A | 8/1996 | Tsuji et al. | | 5,882,339 A | 3/1999 | Beiser et al. |
| 5,569,158 A | 10/1996 | Suzuki et al. | | 5,889,670 A | 3/1999 | Schuler et al. |
| 5,569,159 A | 10/1996 | Anderson et al. | | 5,889,672 A | 3/1999 | Schuler et al. |
| 5,586,262 A | 12/1996 | Komatsu et al. | | 5,892,630 A | 4/1999 | Broome |
| 5,589,854 A | 12/1996 | Tsai | | 5,895,350 A | 4/1999 | Hori |
| 5,591,202 A | 1/1997 | Slater et al. | | 5,897,507 A | 4/1999 | Kortenbach et al. |
| 5,608,451 A | 3/1997 | Konno et al. | | 5,897,525 A | 4/1999 | Dey et al. |
| 5,609,561 A | 3/1997 | Uehara | | 5,907,487 A | 5/1999 | Rosenberg et al. |
| 5,619,380 A | 4/1997 | Agasawa et al. | | 5,923,018 A | 7/1999 | Kameda et al. |
| 5,622,528 A | 4/1997 | Hamano et al. | | 5,928,136 A | 7/1999 | Barry |
| 5,631,695 A | 5/1997 | Nakamura et al. | | 5,929,607 A | 7/1999 | Rosenberg et al. |
| 5,633,203 A | 5/1997 | Adair | | 5,929,846 A | 7/1999 | Rosenberg et al. |
| 5,643,203 A | 7/1997 | Beiser et al. | | 5,929,900 A | 7/1999 | Yamanaka |
| 5,645,075 A | 7/1997 | Palmer et al. | | 5,929,901 A | 7/1999 | Adair et al. |
| 5,647,840 A | 7/1997 | D'Amelio et al. | | 5,931,833 A | 8/1999 | Silverstein |
| 5,658,238 A | 8/1997 | Suzuki et al. | | 5,933,809 A | 8/1999 | Hunt et al. |
| 5,667,477 A | 9/1997 | Segawa | | 5,935,085 A | 8/1999 | Welsh et al. |
| 5,674,182 A | 10/1997 | Suzuki et al. | | 5,936,778 A | 8/1999 | Miyano et al. |
| 5,674,197 A | 10/1997 | van Muiden et al. | | 5,941,817 A | 8/1999 | Crawford |
| 5,685,823 A | 11/1997 | Ito et al. | | 5,950,168 A | 9/1999 | Simborg et al. |
| 5,685,825 A | 11/1997 | Takase et al. | | 5,951,462 A | 9/1999 | Yamanaka |
| 5,691,853 A | 11/1997 | Miyano | | 5,951,464 A * | 9/1999 | Takahashi et al. ............ 600/176 |
| 5,695,450 A | 12/1997 | Yabe et al. | | 5,956,416 A | 9/1999 | Tsuruoka et al. |
| 5,698,866 A | 12/1997 | Doiron et al. | | 5,956,689 A | 9/1999 | Everhart |
| 5,702,349 A | 12/1997 | Morizumi | | 5,956,690 A | 9/1999 | Haggerson et al. |
| 5,702,754 A | 12/1997 | Zhong | | 5,959,613 A | 9/1999 | Rosenberg et al. |
| 5,703,724 A | 12/1997 | Miyano | | 5,976,070 A | 11/1999 | Ono et al. |
| 5,704,371 A | 1/1998 | Shepard | | 5,976,074 A | 11/1999 | Moriyama |
| 5,704,896 A | 1/1998 | Fukunishi et al. | | 5,980,454 A | 11/1999 | Broome |
| 5,708,482 A | 1/1998 | Takahashi et al. | | 5,980,468 A | 11/1999 | Zimmon |
| 5,721,566 A | 2/1998 | Rosenberg et al. | | 5,986,693 A | 11/1999 | Adair et al. |
| 5,724,068 A | 3/1998 | Sanchez et al. | | 5,991,729 A | 11/1999 | Barry et al. |
| 5,728,045 A | 3/1998 | Komi | | 5,991,730 A | 11/1999 | Lubin et al. |
| 5,739,811 A | 4/1998 | Rosenberg et al. | | 5,999,168 A | 12/1999 | Rosenberg et al. |
| 5,740,801 A | 4/1998 | Branson | | 6,002,425 A | 12/1999 | Yamanaka et al. |
| 5,746,696 A | 5/1998 | Kondo | | 6,007,482 A | 12/1999 | Madni et al. |
| 5,764,809 A | 6/1998 | Nomami et al. | | 6,007,531 A | 12/1999 | Snoke et al. |
| 5,767,839 A | 6/1998 | Rosenberg | | 6,014,630 A | 1/2000 | Jeacock et al. |
| 5,779,686 A | 7/1998 | Sato et al. | | 6,015,088 A | 1/2000 | Parker et al. |
| 5,781,172 A | 7/1998 | Engel et al. | | 6,017,322 A | 1/2000 | Snoke et al. |
| 5,788,714 A | 8/1998 | Ouchi | | 6,020,875 A | 2/2000 | Moore et al. |
| 5,789,047 A | 8/1998 | Sasaki et al. | | 6,020,876 A | 2/2000 | Rosenberg et al. |
| 5,793,539 A | 8/1998 | Konno et al. | | 6,026,363 A | 2/2000 | Shepard |
| 5,805,140 A | 9/1998 | Rosenberg et al. | | 6,030,360 A | 2/2000 | Biggs |
| 5,810,715 A | 9/1998 | Moriyama | | 6,032,120 A | 2/2000 | Rock et al. |
| 5,812,983 A | 9/1998 | Kumagai | | 6,039,728 A | 3/2000 | Berlien et al. |
| 5,819,736 A | 10/1998 | Avny et al. | | 6,043,839 A | 3/2000 | Adair et al. |
| 5,820,591 A | 10/1998 | Thompson et al. | | 6,050,718 A | 4/2000 | Schena et al. |
| 5,821,466 A | 10/1998 | Clark et al. | | 6,057,828 A | 5/2000 | Rosenberg et al. |

| | | | |
|---|---|---|---|
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,101 A * | 6/2000 | Tatsuno et al. ............ 600/112 |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,100,874 A | 8/2000 | Schena et al. |
| 6,104,382 A | 8/2000 | Martin et al. |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamuka |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,238,799 B1 | 5/2001 | Opolski |
| 6,241,668 B1 | 6/2001 | Herzog |
| 6,260,994 B1 | 7/2001 | Matsumoto et al. |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,366,799 B1 | 4/2002 | Acker et al. |
| 6,381,029 B1 | 4/2002 | Tipirneni |
| 6,398,724 B1 | 6/2002 | May et al. |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,489,987 B1 | 12/2002 | Higuchi et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,520,908 B1 | 2/2003 | Ikeda et al. |
| 6,524,234 B2 | 2/2003 | Ouchi |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,558,317 B2 | 5/2003 | Takahashi et al. |
| 6,561,971 B1 | 5/2003 | Akiba |
| 6,565,507 B2 | 5/2003 | Kamata et al. |
| 6,574,629 B1 | 6/2003 | Cooke, Jr. et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B2 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Omori et al. |
| 6,682,479 B1 | 1/2004 | Takahashi et al. |
| 6,685,631 B2 | 2/2004 | Minami |
| 6,686,949 B2 | 2/2004 | Kobayashi et al. |
| 6,690,409 B1 | 2/2004 | Takahashi |
| 6,690,963 B2 | 2/2004 | Ben-Haim et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B1 | 3/2004 | Benaron et al. |
| 6,715,068 B1 | 3/2004 | Kazunori |
| 6,716,162 B2 | 4/2004 | Hakamata |
| 6,728,599 B2 | 4/2004 | Wang et al. |
| 6,730,018 B2 | 5/2004 | Takase |
| 6,734,893 B1 | 5/2004 | Hess et al. |
| 6,736,773 B2 | 5/2004 | Wendlandt et al. |
| 6,743,240 B2 | 6/2004 | Smith et al. |
| 6,749,559 B1 | 6/2004 | Krass et al. |
| 6,749,560 B1 | 6/2004 | Konstorum et al. |
| 6,749,561 B2 | 6/2004 | Kazakevich |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,414 B1 | 8/2004 | McStravick et al. |
| 6,785,593 B2 | 8/2004 | Wang et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |

| | | | |
|---|---|---|---|
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayahi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,821 B2 | 9/2005 | Abe et al. |
| 6,943,822 B2 | 9/2005 | Iida et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,248 B2 | 9/2005 | Rudischhauser et al. |
| 6,950,691 B2 | 9/2005 | Uchikubo |
| 6,954,311 B2 | 10/2005 | Amanai |
| 6,955,671 B2 | 10/2005 | Uchikubo |
| 6,956,703 B2 | 10/2005 | Saito |
| 6,961,187 B2 | 11/2005 | Amanai |
| 6,962,564 B2 | 11/2005 | Hickle |
| 6,963,175 B2 | 11/2005 | Archenhold et al. |
| 6,964,662 B2 | 11/2005 | Kidooka et al. |
| 6,967,673 B2 | 11/2005 | Ozawa et al. |
| 6,974,466 B2 | 12/2005 | Ahmed et al. |
| 6,975,968 B2 | 12/2005 | Nakamitsu et al. |
| 6,976,954 B2 | 12/2005 | Takahashi |
| 6,977,053 B2 | 12/2005 | Mukasa et al. |
| 6,977,670 B2 | 12/2005 | Takahashi et al. |
| 6,980,227 B2 | 12/2005 | Iida et al. |
| 6,980,921 B2 | 12/2005 | Anderson et al. |
| 6,981,945 B1 | 1/2006 | Sarvazyan et al. |
| 6,982,740 B2 | 1/2006 | Adair et al. |
| 6,984,206 B2 | 1/2006 | Kumei et al. |
| 6,985,183 B2 | 1/2006 | Jan et al. |
| 6,986,686 B2 | 1/2006 | Shibata et al. |
| 6,994,668 B2 | 2/2006 | Miyano |
| 6,994,704 B2 | 2/2006 | Qin et al. |
| 7,001,330 B2 | 2/2006 | Kobayashi |
| 7,008,376 B2 | 3/2006 | Ikeda et al. |
| 7,413,543 B2 | 8/2008 | Banik |
| 7,537,561 B2 * | 5/2009 | Yamaya et al. ............ 600/106 |
| 7,578,786 B2 * | 8/2009 | Boulais et al. ............ 600/142 |
| 7,591,783 B2 * | 9/2009 | Boulais et al. ............ 600/142 |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0163575 A1 | 11/2002 | Ayame et al. |
| 2002/0193662 A1 | 12/2002 | Belson |
| 2002/0193664 A1 | 12/2002 | Ross et al. |
| 2003/0032863 A1 | 2/2003 | Kazakevich |
| 2003/0045778 A1 | 3/2003 | Ohline et al. |
| 2003/0065250 A1 | 4/2003 | Chiel et al. |
| 2003/0069897 A1 | 4/2003 | Roy et al. |
| 2003/0149338 A1 | 8/2003 | Francois et al. |
| 2003/0181905 A1 | 9/2003 | Long |
| 2003/0227547 A1 | 12/2003 | Iddan |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Meada et al. |
| 2004/0073085 A1 | 4/2004 | Ikeda et al. |
| 2004/0143159 A1 | 7/2004 | Wendlandt |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0075538 A1 * | 4/2005 | Banik et al. ............ 600/141 |
| 2005/0119527 A1 | 6/2005 | Banik |
| 2005/0192476 A1 | 9/2005 | Homan et al. |
| 2005/0197861 A1 | 9/2005 | Omori et al. |
| 2005/0200698 A1 | 9/2005 | Amling et al. |
| 2005/0203341 A1 | 9/2005 | Welker et al. |
| 2005/0203418 A1 | 9/2005 | Yamada et al. |
| 2005/0205958 A1 | 9/2005 | Taniguchi et al. |
| 2005/0207645 A1 | 9/2005 | Nishimura et al. |
| 2005/0209509 A1 | 9/2005 | Belson |
| 2005/0225872 A1 | 10/2005 | Uzawa et al. |
| 2005/0226508 A1 | 10/2005 | Gotohda |
| 2005/0228221 A1 | 10/2005 | Hirakawa |
| 2005/0228222 A1 | 10/2005 | Furumi |
| 2005/0228227 A1 | 10/2005 | Weber |
| 2005/0228697 A1 | 10/2005 | Funahashi |
| 2005/0231591 A1 | 10/2005 | Abe |
| 2005/0234507 A1 | 10/2005 | Geske et al. |
| 2005/0243169 A1 | 11/2005 | Ono et al. |
| 2005/0247081 A1 | 11/2005 | Sakata et al. |
| 2005/0250983 A1 | 11/2005 | Tremaglio et al. |
| 2005/0251112 A1 | 11/2005 | Danitz et al. |
| 2005/0251998 A1 | 11/2005 | Bar-Or et al. |
| 2005/0253044 A1 | 11/2005 | Kuriyama |
| 2005/0256370 A1 | 11/2005 | Fujita |
| 2005/0256373 A1 | 11/2005 | Bar-Or et al. |
| 2005/0256377 A1 | 11/2005 | Deppmeier et al. |
| 2005/0256424 A1 | 11/2005 | Zimmon |
| 2005/0264687 A1 | 12/2005 | Murayama |
| 2005/0267417 A1 | 12/2005 | Secrest et al. |
| 2005/0271340 A1 | 12/2005 | Weisburg et al. |
| 2005/0272978 A1 | 12/2005 | Brunnen et al. |
| 2005/0273085 A1 | 12/2005 | Hinmane et al. |
| 2005/0288545 A1 | 12/2005 | Matsumoto et al. |
| 2005/0288546 A1 * | 12/2005 | Sonnenschein et al. ...... 600/101 |
| 2005/0288553 A1 | 12/2005 | Sugimoto |

FOREIGN PATENT DOCUMENTS

| | | |
|---|---|---|
| EP | 0 075 153 B1 | 3/1983 |
| EP | 0 437 229 A1 | 7/1991 |
| EP | 0 689 851 A1 | 1/1996 |
| EP | 0 728 487 B1 | 8/1996 |
| EP | 1 300 883 A2 | 4/2003 |
| EP | 1421894 A2 | 5/2004 |
| EP | 1 433 412 A | 6/2004 |
| JP | 58-78635 A | 5/1983 |
| JP | 05-31071 A | 2/1993 |
| JP | 05-091972 A | 4/1993 |
| JP | 06-105800 | 4/1994 |
| JP | 06-254048 A | 9/1994 |

| | | | |
|---|---|---|---|
| JP | 07-8441 A | 1/1995 |
| JP | 10-113330 A | 5/1998 |
| JP | 10-286221 A | 10/1998 |
| JP | 11-216113 A | 8/1999 |
| JP | 2001 128933 A | 5/2001 |
| JP | 3219521 B2 | 8/2001 |
| JP | 2002 078675 A | 3/2002 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 3372273 B2 | 11/2002 |
| JP | 2003-75113 A | 3/2003 |
| JP | 2002 007134 A | 7/2003 |
| JP | 3482238 B2 | 10/2003 |
| WO | WO 93/13704 A1 | 7/1993 |
| WO | WO 03/097156 A | 11/2003 |
| WO | WO 2004/016310 A2 | 2/2004 |
| WO | WO 2005/023082 A2 | 3/2005 |
| WO | 2006025058 A1 | 3/2006 |

\* cited by examiner

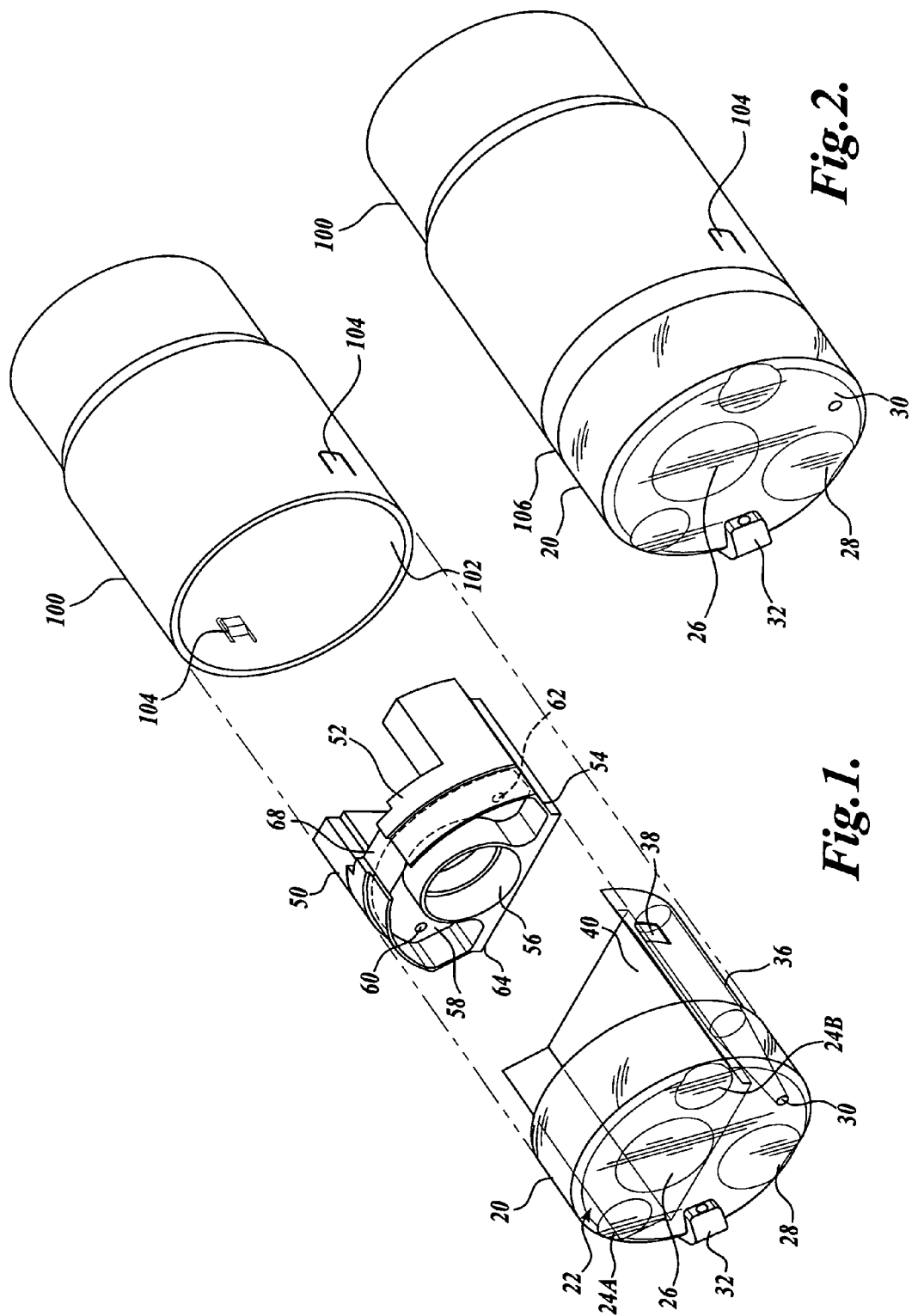

IMAGING ASSEMBLY WITH TRANSPARENT DISTAL CAP

FIELD OF THE INVENTION

The present invention relates to medical devices, and in particular to medical devices that produce images of internal body tissues.

BACKGROUND

As an alternative to performing more invasive types of procedures in order to examine, diagnose, and treat internal body tissues, many physicians are using minimally invasive devices such as catheters and endoscopes to perform such tasks. Such medical devices are inserted into the body and routed to a point of interest in order to allow the physician to view and treat the internal body tissues. Generally such devices include some sort of image producing mechanism, such as a fiber optic imaging guide that transmits an image along a bundle of fibers to a proximal camera or eyepiece. Alternatively, video endoscopes or catheters include a small image sensor that produces images of the tissue electronically.

In a conventional endoscope, the distal tip of the device is often opaque and includes one or more windows or lenses that are used for the delivery of illumination light and an objective lens assembly for either transmitting an image to the proximal end of the endoscope or for focusing an image on an image sensor. While the opaque distal tips have generally been proven to work well, improvements can be made.

SUMMARY

The invention described here relates generally to an imaging assembly for a medical device and in particular, with respect to one embodiment, includes a transparent distal cap and an image sensor insert that is fitted into the distal cap. The image sensor insert includes a cooling channel that is thermally coupled to one or more illumination sources in the image sensor insert. In one embodiment, opaque shields may be added within the imaging assembly to prevent stray illumination light from leaking to the image sensor.

In one embodiment of the present invention, the imaging assembly is partially fitted within a metal ring of an articulation joint to shield circuitry in the imaging assembly.

In accordance with another embodiment of the present invention, the distal cap includes one or more molded lenses.

In accordance with another embodiment of the present invention, a thermistor is used to sense the temperature of the illumination sources. In one embodiment, the thermistor shares a common lead with the illumination sources and electronics that read a voltage across the thermistor compensate for a voltage on the common lead produced by current in the illumination sources.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is an exploded view of an imaging assembly in accordance with one embodiment of the present invention;

FIG. 2 shows the imaging assembly of FIG. 1 in an assembled configuration;

DETAILED DESCRIPTION

Figure 3:
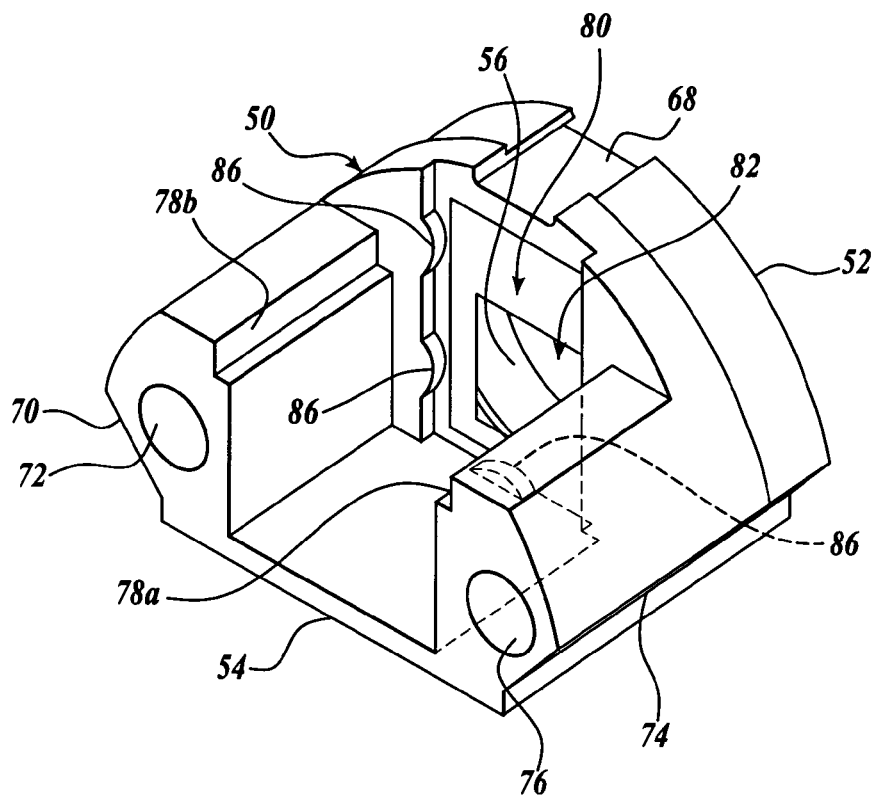
FIG. 3 is a rear view of an image sensor insert that is a component of the imaging assembly in accordance with an embodiment of the present invention.

As indicated above, the present invention is an imaging assembly for use in an endoscope or other medical imaging device. Although the disclosed embodiment of the invention is for use in an endoscope such as a colonoscope, bronchoscope, duodenoscope, and the like, it will be appreciated that the present invention is not limited to endoscopes but could be used in other medical imaging devices, such as catheters, for use in vascular, urinary, reproductive, ear, nose, and throat, applications, or the like.

FIG. 1 is an exploded view of an imaging assembly for an endoscope in accordance with an embodiment of the present invention. The imaging assembly includes a transparent distal cap 20 that is positioned at the distal end of the endoscope. An image sensor insert 50 is received within the cap 20. The distal cap 20 and the image sensor insert 50 are secured to a distal portion of the endoscope shaft. In one embodiment, the assembly is secured to the distal most ring 100 of an articulation joint of the type that includes a series of linked metal or conductive rings (not shown) that allow the endoscope to bend in a desired direction under tension of one or more control wires.

In one embodiment, the transparent distal cap 20 is made of a plastic material such as clear polycarbonate. The cap 20 has a distal face 22 having a number of features molded therein. The distal face 22 includes a pair of windows 24a and 24b that allow illumination from an illumination source, such as LEDs positioned behind the windows, to reach the tissue to be imaged by the endoscope. In the embodiment shown, the windows 24a, 24b are flat, circular areas of clear plastic. However, lenses could be molded into the distal cap to change the pattern of illumination light distribution if desired.

In the embodiment shown, the windows 24a and 24b extend all the way to the outer rim of the distal cap 20. This allows the rim to be made smaller and to be smoothly rounded in order to provide increased patient comfort and reduce the chance of injury to the patient.

Positioned generally between the windows 24a and 24b is an opening 26 that is provided to receive an objective lens assembly for the image sensor. Below the opening 26 for the lens assembly is an opening 28 that serves as an entrance to a working channel of the endoscope. In one embodiment, the rim of the cap 20 is beveled in the area of the opening 28 to the working channel to provide a rounded edge and improve patient comfort. A port 30 is adjacent the opening 28 to the working channel and is connected to a tube (not shown) in the endoscope for application of a jet wash liquid from the endoscope. A second port 32 is positioned at the end of a nozzle that extends smoothly out from the edge of the distal face 22 and bends over to distal face to direct water across the front face of the objective lens assembly that is within the opening 26 and/or the windows 24a, 24b that are in front of the illumination sources. In addition, air or a gas can be delivered from the port 32 for insufflation of the patient as needed.

The proximal end of the distal cap 20 includes a stepped region 36 having a diameter slightly smaller than the diameter of the distal region of the cap 20. Therefore, the proximal region 36 of the distal cap 20 can fit within an opening 102 of the distalnost ring 100 of the articulation joint. The side surface of the proximal region 36 also includes one or more notches 38 that receive corresponding tabs 104 on the ring 100 of the articulation joint. The ring 100 may cover the majority of the sensor circuitry disposed at the distal tip of the endoscope, thereby providing electrical shielding to the circuitry when this ring is connected to an electrical ground.

The proximal end of the cap 20 also includes a flat receiving surface 40 that is oriented in a direction generally perpendicular to the plane of the distal face 22. The receiving surface 40 divides the distal cap into an upper portion and a lower portion. As will be described in further detail below, the image sensor insert 50 is slideable on the receiving surface 40 such that the components it holds are positioned behind the distal face 22 of the cap 20.

The image sensor insert 50 comprises a generally semicircular component with a rounded upper portion 52 and a generally flat bottom surface 54. The bottom surface 54 rests on the receiving surface 40 of the distal cap 20 while the rounded upper portion 52 fits behind the upper portion of the distal face 22 of the cap 20. In the center of the image sensor insert 50 is a cylindrical bore 56 into which an image sensor objective lens assembly (not shown) is fitted. The cylindrical bore 56 also includes a shoulder or lip therein to limit how far the objective lens assembly can be inserted into the bore 56 in order to aid in focusing the lens assembly. In addition, the shoulder or lip helps to prevent stray illumination light from reaching the image sensor.

In one embodiment, the image sensor objective lens assembly is formed in a lens barrel that secures the lenses and other components together as a group. The barrel is adhesively or otherwise secured in the cylindrical bore 56 at a position that focuses the light onto the image sensor. In another embodiment, the lenses and other components of the objective lens assembly can be held directly in the cylindrical bore 56 without a lens barrel.

Surrounding the bore 56 is a semicircular cooling channel 58 in which a cooling liquid or gas is passed. The cooling liquid or gas enters and exits at a pair of ports 60, 62 at opposite ends of the channel. The ports 60, 62 are coupled to tubes within the endoscope that deliver and return the cooling liquid or gas. A lip 64 surrounds the inner perimeter of the cooling channel 58 and provides a support for a circuit board that is seated within the channel 58, as will be described in further detail below. A channel or notch 68 extends proximally from the front of the image sensor insert 50 over the curved upper portion 52 of the image sensor insert 50 to allow passage of a current-carrying circuit or wires that carry current to the illumination devices and a thermistor on a circuit board, as will be described in further detail below.

FIG. 2 illustrates the distal cap 20 fitted within the distal ring 100 of an articulation joint. The tabs 104 on the ring fit within the corresponding notches 38 on the distal cap 20, thereby securing the two parts together.

In final assembly, an outer sheath (not shown) covers the articulation joint 100 and a seam 106 where the articulation joint meets the distal cap 20. In one embodiment, the sheath is made of a biocompatible polymer such as polyurethane or the like.

Figure 5:
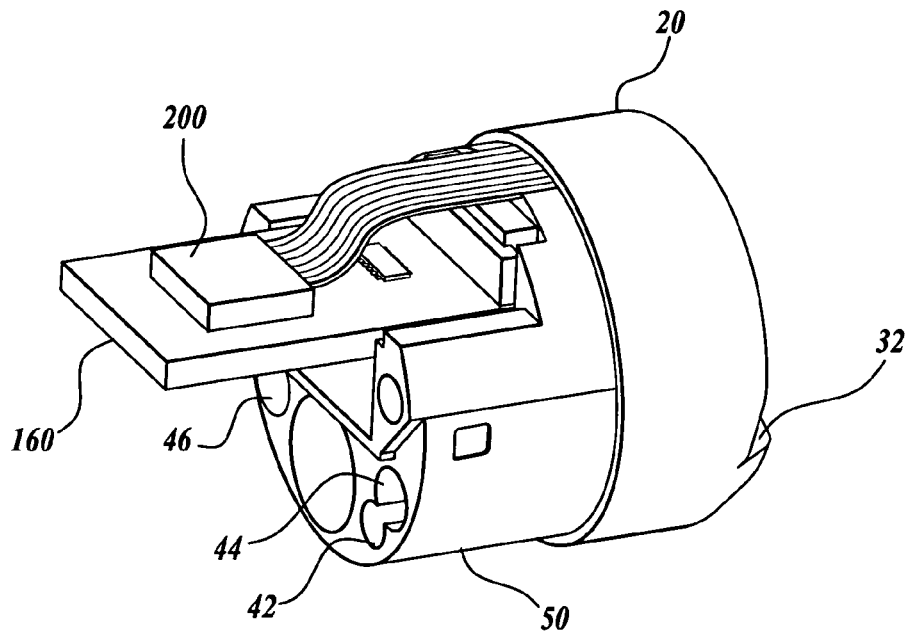
FIG. 5 shows an imaging assembly including a distal cap, image sensor insert, and a circuit board in an assembled configuration in accordance with an embodiment of the present invention.

FIG. 3 illustrates further detail of the image sensor insert 50 when viewed from the rear or proximal end. Positioned on either side of the image sensor insert is a pair of proximally extending legs 70 and 74. Each leg 70, 74 has a corresponding lumen 72, 76 therein that delivers a cooling liquid or gas to the two ports 60, 62 that open to the cooling channel 58. The lumen 76 is in fluid communication with the port 60 and the lumen 72 is in fluid communication with the port 62 as shown in FIG. 1. Each of the legs 70, 74 also includes an inwardly facing step 78a, 78b that provides a support for a circuit board to be secured to the image sensor insert 50 as can be seen in FIG. 5.

The image sensor insert 50 also includes a recessed, rectangular image sensor receiving surface 80 that is oriented in the same plane as the distal face 22 of the distal cap 20. The image sensor receiving surface 80 has a smaller circular or rectangular aperture 82 therein which opens to the cylindrical bore 56. The area surrounding the aperture 82 is generally flat so that an image sensor such as a CMOS or CCD imager (not shown) can be secured thereto with an adhesive or the like. In one embodiment, the aperture is larger than the area that forms the image on the image sensor so that no imaging pixels are wasted.

In the embodiment shown, one or more alignment bosses 86 are positioned at the sides of the image sensor receiving surface 80. The bosses 86 are configured as small semicircular protrusions on two sides of the image sensor receiving surface 80 and serve to align an image sensor positioned therein.

Figure 4:
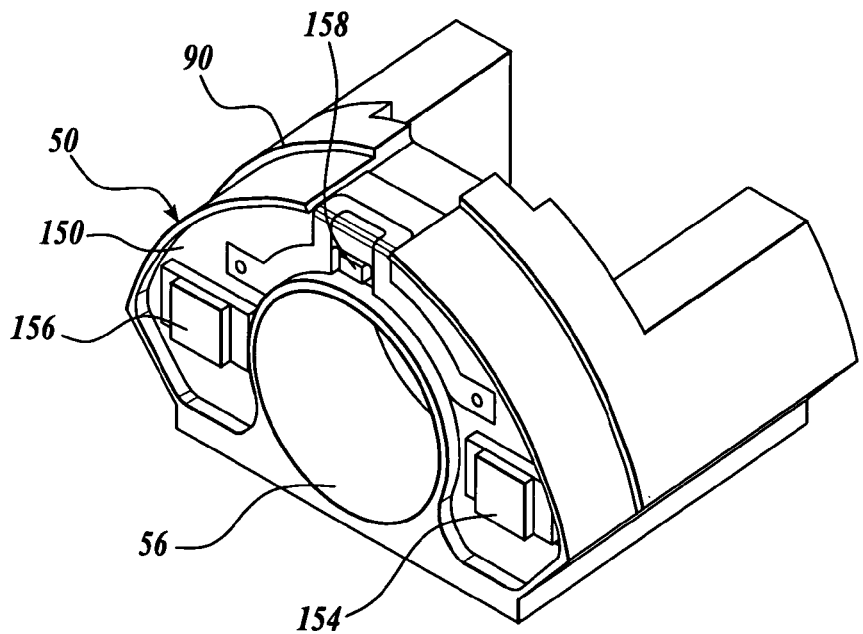
FIG. 4 is a front isometric view of an image sensor insert in accordance with an embodiment of the present invention.

FIG. 4 shows further detail of the image sensor insert 50 from the front or distal end. As indicated above, the image sensor insert has a shape that is designed to be slideably received behind the distal face of the distal cap 20. A raised lip 90 over the curved upper portion 52 of the insert 50 limits the depth to which the insert can be fitted into the distal cap 20. In the embodiment shown in FIG. 4, a semicircular thermal clad circuit board 150 is shown seated on the rim 64 surrounding the cooling channel 58. The circuit board 150 supports one or more illumination LEDs 154 and 156 as well as a thermistor 158. The thermistor is generally positioned above the cylindrical bore 56 that receives the imager objective lens assembly.

In one embodiment, leads that provide power to the LEDs 154, 156 as well as leads that connect to the thermistor 158 are provided on a rigid circuit board or by direct connect wires. In another embodiment, leads that provide power to the LEDs 154, 156 as well as leads that connect to the thermistor 158 are included on a flex circuit. The flex circuit is secured to the circuit board 150 and extends over the top of the image sensor insert through the channel 68 as shown in FIGS. 1 and 3.

As will be appreciated by viewing the bottom of the image sensor insert 50 shown in FIG. 4, the bottom of the image sensor insert 50 is generally flat and does not contain any openings in order to protect the image sensor and associated electronics from dirt, moisture, etc., during assembly and use. In one embodiment, the image sensor insert 50 is molded from a plastic material such as ABS acetyl butyl styrene.

FIG. 5 shows the image sensor insert 50 fitted within the distal cap 20. In addition, a circuit board 160 is seated in the steps 78a, 78b of the image sensor insert as shown in FIG. 3. In one embodiment, the circuit board 160 is bonded to the steps 78a, 78b of the proximally extending legs 70, 74 with an adhesive or the like. Also shown in FIG. 5 are the lumens in the lower portion of the distal cap 20 that deliver the gas/water to the ports on the distal face. A lumen 42 delivers water to the lens wash port 32 and a lumen 44 delivers the insufflation gas to the port 32. A lumen 46 delivers water to the jet wash port 30.

Figure 6A:
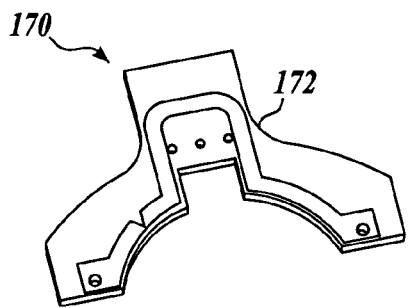
FIGS. 6A-6C illustrate a flex circuit and thermal clad circuit board used in an imaging assembly in accordance with an embodiment of the present invention.

FIG. 6A shows a top side of a flex circuit 170 that provides power to the LEDs and connects to the thermistor. On the top of the flex circuit 170 is a series interconnect 172 that connects each of the illumination LEDs in series.

Figure 6B:
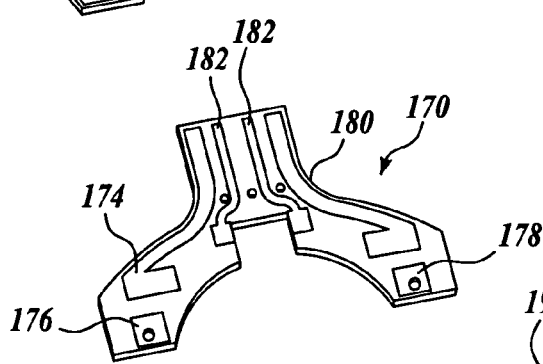

The bottom side of the flex circuit 170 is shown in FIG. 6B. The bottom of the flex circuit includes a trace 174 that delivers current to the LEDs. A via 176 passes the current to the top side of the flex circuit and to the series interconnect 172. A second via 178 returns the current from the top side of the flex circuit to the bottom side of the flex circuit. A trace 180 returns the current delivered to the LEDs to its source electronics. The bottom side of the flex circuit also includes a pair of traces 182 that connect the thermistor to a circuit that measures the temperature of the distal tip. If the temperature is too high, the current to the illumination LEDs can be reduced or the procedure may be halted. It will be recognized that the pattern of traces on the flex circuit is exemplary of an embodiment of the present invention.

Figure 6C:
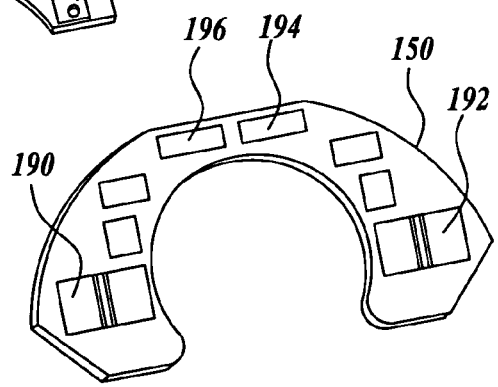

FIG. 6C illustrates the thermal clad circuit board 150 on which the illumination LEDs and thermistor are mounted. As described above, the thermal clad circuit includes two pairs of pads 190, 192 upon which the illumination LEDs are bonded. The circuit board also includes interconnects 194 for connecting the power to the LEDs. In addition, the circuit board includes a pair of pads 196 positioned between the LEDs upon which the thermistor is bonded. The rear surface of the circuit board 150 is clad with a heat conductive material such as copper, gold, silver, aluminum or other biocompatible material to transfer heat from the LEDs to the cooling liquid or gas flowing in the cooling channel 58. In some embodiments, the front surface of the circuit board 150 may be coated with a reflective material such as aluminum to direct light emitted from the LEDs distally.

As shown in FIG. 5, the other end of the flex circuit 170 is preferably inserted into a zero insertion force flex connector 200 on the circuit board 160. The zero insertion force connector 200 provides a simple way to assemble the distal tip without the use of complicated soldering operations or jumpers. In one embodiment, the thermistor and the LEDs share a common return lead extending from the circuit board 160 in the distal tip to external electronics in a remotely located control cabinet in order to reduce the number of wires in the endoscope. However, current from the LEDs can induce a voltage on this common lead that is read at the control electronics as appearing across the thermistor. This increased voltage can therefore make it appear as if the thermistor is cooler than it actually is. To compensate for this, the electronics can compare the voltage across the thermistor with a reference voltage that is based on the maximum drive current of the LEDs and the resistance of the common lead. Alternatively, the thermistor can have its own power and return leads to obtain more accurate readings from the thermistor.

As it will be appreciated from the above, the present invention provides a simple assembly for housing the imaging components of an imaging endoscope or other medical imaging device. Because the distal cap is made of a transparent plastic material, more light provided by the illumination components is able to reach the target tissue. Furthermore, because the distal tip is transparent, adhesive connections within the assembly can be cured by the application of curing energies, such as ultraviolet light, into the distal tip.

Although the present invention is described with respect to its currently preferred embodiments, it will be appreciated by those skilled in the art that changes could be made. For example, it is possible to place other components on the circuit board 150. For example, it may be desirable to place one or more additional LEDs on the board or elsewhere in the distal cap 20 to facilitate transillumination. Transillumination involves lighting the distal tip of an endoscope or catheter so that it can be seen from outside the body. A light source used for transillumination should have good tissue penetration such as red LEDs. The light source may be pulsed or strobed to aid in its detection. Power to the transillumination LEDs can be provided through the flex circuit. During transillumination, it may be desirable to darken the ambient light surrounding the patient and to disable any flickering light sources such as video display screens or the like in order to detect the light emitting from the distal tip.

Figure 7:
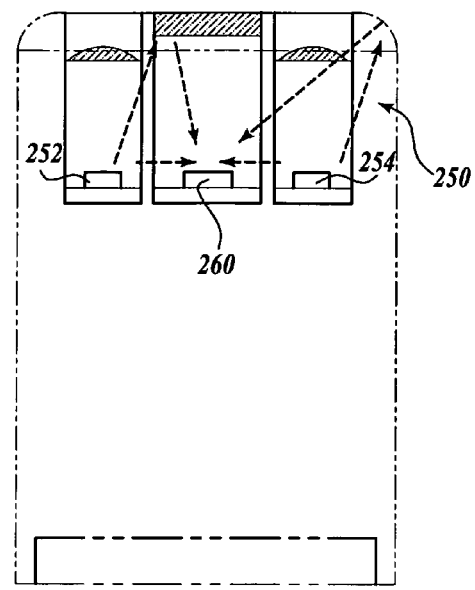
FIG. 7 illustrates how stray light from an illumination source can leak into an image sensor.
Figure 8:
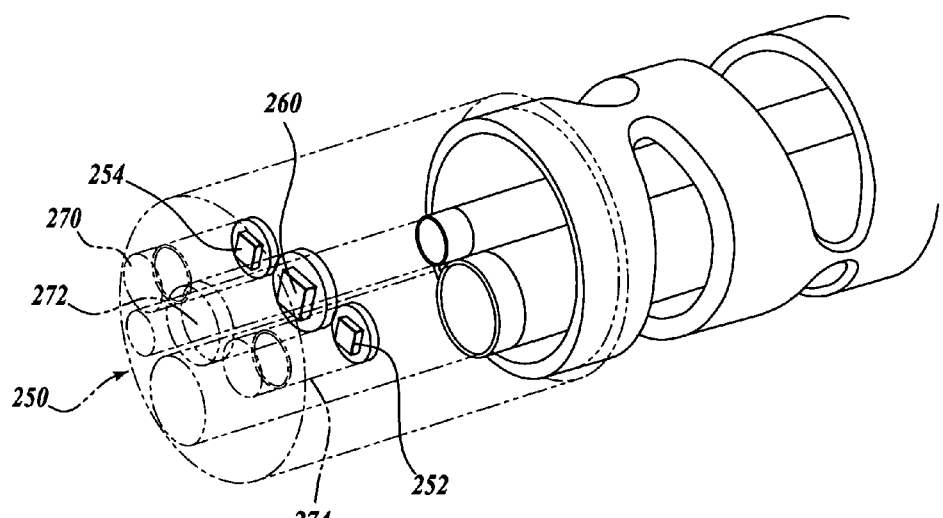
FIG. 8 illustrates how opaque sleeves can reduce the stray light in accordance with another embodiment of the present invention.

In some situations, light from the illumination sources may leak to the image sensor when a transparent distal cap is used. For example, FIG. 7 illustrates a transparent distal cap 250 on an endoscope or other medical device. The distal tip includes LED illumination sources 252 and 254. Light from those sources can reflect off the surfaces of the distal cap and otherwise leak to an image sensor 260.

In accordance with another aspect of the present invention, opaque shields 270, 272, 274 are added in front of the illumination sources and/or the image sensor to reduce the light leakage and prevent light from escaping in a direction other than through the windows in the distal cap. The opaque shield 274 in front of the image sensor 260 reduces light leaking indirectly to the image sensor. The opaque shields may be molded cylinders or other shapes and made from a black or other opaque plastic material. Alternatively, the shields may be made from an opaque film or coating placed in the cavities of the distal end cap. With the shields in place, only illumination light that is reflected off a tissue sample reaches the image sensor.

Although the present invention has been described with respect to disclosed embodiments, it will be appreciated that changes may be made without departing from the scope of the invention. For example, the illumination sources may comprise incandescent lights or fiber optic light guides to deliver light produced from an external source. Therefore, it is intended that the scope of the invention be determined from the following claims and equivalents thereof.

The embodiments of the invention in which an exclusive property or privilege is claimed are defined as follows:

1. An assembly for an imaging medical device, comprising:
   a transparent distal cap, said transparent distal cap having a distal face surface with a perimeter surrounding an entirety of the distal face surface; and
   an image sensor insert that is fitted within the transparent distal cap, the image sensor insert including:
   one or more illumination sources;
   a cooling channel for removing heat from the one or more illumination sources;
   a cylindrical bore adapted to accommodate one or more imaging lenses; and
   an image sensor;
   wherein the transparent distal cap includes one or more integral windows positioned in front of the one or more illumination sources, wherein the one or more windows have an edge that extends to the perimeter.

2. The assembly of claim 1, wherein the image sensor insert also includes a thermistor thermally coupled to the one or more illumination sources.

3. The assembly of claim 2, wherein the thermistor is positioned between the one or more illumination sources.

4. The assembly of claim 1, wherein the one or more illumination sources are LEDs.

5. The assembly of claim 4, wherein the image sensor insert includes a flex circuit that delivers current to the LEDs.

6. The assembly of claim 5, wherein the image sensor insert includes a channel positioned over the image sensor insert in which the flex circuit is positioned.

7. The assembly of claim 1, wherein the transparent distal cap is molded of a clear plastic material.

8. The assembly of claim 1, wherein the edge of the transparent distal cap is rounded.

9. The assembly of claim 1, further including a transillumination light source positioned behind the transparent distal cap that produces light to locate a distal tip of the medical device.

10. The assembly of claim 9, wherein the transillumination light source is an LED.

11. The assembly of claim 10, wherein the transillumination LED produces red light.

12. The assembly of claim 1, wherein the image sensor insert is generally semicircular in shape.

13. The assembly of claim 1, wherein the transparent distal cap further includes an opening that serves as an entrance to a working channel and wherein a rim of the transparent distal cap is beveled in the area of the opening.

\* \* \* \* \*